United States Patent [19]

Stürmer

[11] 3,943,246

[45] Mar. 9, 1976

[54] ORGANIC COMPOUNDS

[75] Inventor: Egon Stürmer, Riehen, Switzerland

[73] Assignee: Sandoz Ltd., Basel, Switzerland

[22] Filed: Aug. 28, 1974

[21] Appl. No.: 501,336

Related U.S. Application Data

[63] Continuation of Ser. No. 376,410, July 5, 1973, abandoned.

[30] Foreign Application Priority Data

July 10, 1972 Switzerland.................... 10303/72
Oct. 25, 1972 Switzerland.................... 15618/72

[52] U.S. Cl. .............................................. 424/177
[51] Int. Cl.² ....................................... A61K 37/00

[58] Field of Search .................................. 424/177

[56] References Cited
OTHER PUBLICATIONS

Pharmakopsychiat, 5 (1972), pp. 187–190, by L. Lidberg.

*Primary Examiner*—Elbert L. Roberts
*Attorney, Agent, or Firm*—Gerald D. Sharkin; Robert S. Honor

[57] ABSTRACT

This invention concerns a novel use of oxytocin and desamino-oxytocin for treating impotency in the human male.

6 Claims, No Drawings

ORGANIC COMPOUNDS

This is a continuation of application Ser. No. 376,410 filed July 5, 1973 now abandoned.

This invention relates to a novel therapeutic use of the known peptides oxytocin and desamino-oxytocin.

At present oxytocin and desamino-oxytocin are used in gynecology. It has now been found that oxytocin and desamino-oxytocin are useful for alleviating impotency especially Impotentia generandi and Impotentia coeundi in the human male as indicated by, for example, the following clinical tests:

During a period of 14 days one buccal tablet containing 100 I.U. oxytocin was administered 3 times a day to each of 16 human males, aged 20 to 63 years. A statistically significant improvement of Impotentia erectionis, a form of Impotentia coeundi, was obtained in 12 of the patients.

Similar results are obtained when 50 I.U. desamino-oxytocin tablets are substituted for the oxytocin tablets.

The dosage of oxytocin or desamino-oxytocin will, of course, vary depending on the mode of administration and condition to be treated.

However, in general, in the case of oxytocin satisfactory results are obtained when administered at a daily dosage of from about 300 to about 1500 I.U. conveniently given in divided doses 2 to 4, preferably however 3, times a day. Preferred dosage forms suitable for oral administration comprise from about 100 to 500 I.U. of oxytocin admixed with a solid or liquid pharmaceutical carrier or diluent.

In the case of desamino-oxytocin, satisfactory results are generally obtained when administered at a daily dosage of from about 150 to about 750 I.U. conveniently given in divided doses 2 to 4, preferably however 3, times a day. Preferred dosage forms suitable for oral administration comprise from about 50 to 250 I.U. of desamino-oxytocin admixed with a solid or liquid pharmaceutical carrier or diluent.

The oxytocin or desamino-oxytocin when employed in the method according to the invention, may be administered in pharmaceutically acceptable acid addition salt form. Such acid addition salt forms exhibit the same order of activity as the free base form and are readily prepared in conventional manner. Such acid addition salt forms are known, and representative acid addition salt forms include the hydrogen maleate, fumarate, and citrate and inorganic salt forms such as the hydrochloride, hydrobromide and sulphate.

Alternatively, the oxytocin or desamino-oxytocin when employed in the method according to the invention may be administered in pharmaceutically acceptable metal complex form. Such complex forms exhibit the same order of activity as the free base form and are readily prepared in conventional manner. Such metal complex forms are known and include the transition metal complex forms such as the Zinc(II) form.

Pharmaceutical compositions containing oxytocin or desamino-oxytocin in association with pharmaceutical carriers or diluents may be employed in the method according to the invention. Such pharmaceutical compositions are known in the art and may be prepared using conventional techniques to be in the form of, for example, capsules, tablets, suppositories, suspensions or solutions for enteral or parenteral administration. Pharmaceutical compositions may contain as well as inert carriers and diluents suitable preserving, stabilizing, wetting, solubilizing, sweetening, flavouring or colouring agents such as cumarin, peppermint oil, citric acid, silicic acid, stearic acid, magnesium stearate, talc, polyvinyl pyrrolidine, mannitol, zinc and protamine sulphate, sodium diphosphate, lactose and sugar. A preferred pharmaceutical composition is a tablet suitable for peroral or buccal administration. A representative tablet contains from 50 to 500 I.U. of oxytocin or from 25 to 250 I.U. of desamino-oxytocin, The following Examples set out details of pharmaceutical compositions suitable for use in the method of the invention, it being understood that further preparations, such as those known in the literature, suitable for use in the method of the invention may be prepared by conventional techniques.

EXAMPLE 1

Oxytocin buccal tablets

Buccal tablets suitable for administration and containing the ingredients described below, may be produced in known manner. The tablets are indicated for use in the treatment of impotency at a dose of 3 tablets daily.

| Ingredients | | |
|---|---|---|
| Oxytocin | 100 | I.U. |
| Cumarin | 0.000040 | g |
| Peppermint oil | 0.000760 | g |
| Stearic acid | 0.0020 | g |
| Talc | 0.0030 | g |
| Polyvinyl pyrrolidone | 0.0050 | g |
| Mannitol | | |
| Zinc sulphate | q.s. | |
| Protamine sulphate | | |
| | 0.20 | g |

EXAMPLE 2

Desamino-oxytocin buccal tablets

Buccal tablets suitable for administration and containing the ingredients described below, may be produced in known manner. The tablets are indicated for use in the treatment of impotency at a dose of 1 to 2 tablets daily.

| Ingredients | | |
|---|---|---|
| Desamino-oxytocin | 50 | I.U. |
| Magnesium stearate | 0.003750 | g |
| Sugar | 0.08750 | g |
| Citric acid anhydrous | | |
| Silicic acid highly dispersed | | |
| Lactose | q.s. | |
| Mannitol | | |
| Sodium diphosphate anhydrous | | |
| | 0.30 | g |

I claim:

1. A method of treating impotency in a human male in need of said treatment which comprises administering oxytocin at a dosage of 300 to 1500 I.U. daily.

2. A method according to claim 1, in which oxytocin is administered in unit dosage form containing from about 50 to about 500 I.U. of oxytocin.

3. A method according to claim 2, in which the unit dosage form is a buccal or peroral tablet.

4. A method of treating impotency in a human male in need of said treatment which comprises administering desamino-oxytocin at a dosage of 150 to 750 I.U. daily.

5. A method according to claim 4, in which the desamino-oxytocin is administered in unit dosage form containing from about 25 to about 250 I.U. of desamino-oxytocin.

6. A method according to claim 5, in which the unit dosage form is a buccal or peroral tablet.

* * * * *